United States Patent [19]

Moore

[11] Patent Number: 5,210,342
[45] Date of Patent: May 11, 1993

[54] PURIFICATION PROCESS

[75] Inventor: Geoffrey J. Moore, Weaverham, England

[73] Assignee: Imperial Chemical Industries Plc, London, England

[21] Appl. No.: 862,717

[22] Filed: Apr. 3, 1992

[30] Foreign Application Priority Data

Apr. 8, 1991 [GB] United Kingdom ................. 9107344

[51] Int. Cl.$^5$ ............................................. C07C 17/38
[52] U.S. Cl. .................................................... 570/179
[58] Field of Search ........................................ 570/179

[56] References Cited

U.S. PATENT DOCUMENTS 4,906,796 3/1990 Yates ................................... 570/134

FOREIGN PATENT DOCUMENTS 2004709 9/1990 Canada .
0154603 4/1982 Fed. Rep. of Germany ...... 570/136

Primary Examiner—Alan Siegel
Attorney, Agent, or Firm—Cushman, Darby & Cushman

[57] ABSTRACT

A process for the removal of chlorocarbon impurities, and in particular chlorofluoromethane from difluoromethane which comprises contacting the impure difluoromethane with an active carbon.

6 Claims, No Drawings

PURIFICATION PROCESS

This invention relates to a process for the removal of chlorine-containing impurities from difluoromethane and in particular to a process for the removal of the toxic impurity chlorofluoromethane from difluoromethane.

In recent years chlorofluorocarbons, which are used on a large scale around the world, have been perceived as having an adverse effect on the ozone layer and/or as contributing to global warming. Chlorofluorocarbons are used, for example, as refrigerants, as foam blowing agents, as cleaning solvents and as propellants for aerosol sprays in which the variety of applications is virtually unlimited. Consequently, attempts have been made to find suitable replacements which will perform adequately in the many applications in which chlorofluorocarbons are used but which will not have the aforementioned harmful effects. The search for suitable replacements has in general centred on fluorocarbons which do not contain chlorine. The hydrofluorocarbon, difluoromethane, also designated HFA 32 is of interest as one such replacement.

However, we have found that a particular problem with many of the processes which we have employed for the production of difluoromethane, for example those based upon chlorine containing starting materials, for example chlorodifluoromethane and dichlorodifluoromethane, is that many chlorine-containing by-products tend to be produced. Some by-products may be easy to separate by distillation whilst others are relatively harmless since they are not toxic and their presence does not greatly alter the physical properties of difluoromethane. However, other by-products, and in particular chlorofluoromethane, is difficult to remove but must be removed or at least reduced to extremely low levels, for example below 10 ppm, because it is highly toxic. Although the boiling point of chlorofluoromethane differs significantly from the boiling point of difluoromethane, we have found that it is extremely difficult to remove the chlorofluoromethane from the difluoromethane to the desired extent by distillation.

According to the present invention there is provided a process for the removal of chlorocarbon impurities from difluoromethane which comprises contacting the impure difluoromethane with an active carbon.

The chlorocarbon impurity is typically a single carbon species, that is a chlorine-containing methane derivative and a preferred embodiment of the invention resides in the removal of chlorofluoromethane from difluoromethane.

The chlorocarbon impurities which may be removed by the process of the invention may contain only carbon and chlorine or they may also contain other atoms, for example hydrogen, fluorine or other halogen atoms.

One particular by-product which is commonly produced in the production of difluoromethane is chlorofluoromethane which, due to its toxicity, must be removed or at least reduced to a very low level, for example to levels below about 10 ppm. The process is particularly useful for the removal of chlorofluoromethane. Other impurities which may be removed include chloromethane, dichloromethane, chlorodifluoromethane and chlorotrifluoromethane.

The term "active" carbon is well known in the art and any material so classified may be employed in the process of the invention. Such materials include the various forms of adsorbent charcoals, for example coconut charcoal, impregnated charcoals and the various products formed by the activation (for example with steam, sulphuric acid or phosphoric acid) of various forms of charcoal, for example coconut or bone charcoal and coal based charcoals. Synthetically produced forms of active carbon may also be used.

We particularly prefer to employ coconut and coconut shell active carbons in the process of the invention, and more particularly steam activated coconut carbons.

The active carbon preferably has a surface area of at least 1000 $m^2/g$, more preferably at least 1050 $m^2/g$ and especially at least 1100 $m^2/g$.

Particular preferred and commercially available active carbons useful in the present invention are 100CTC, 607C and AR2 carbons, (supplied by Sutcliffe Speakman Carbons Ltd).

In the process of the invention, the difluoromethane may be contacted with the active carbon by passing a stream of difluoromethane in the liquid or vapour phase over a fixed bed of active carbon particles. Most effective removal of chlorofluoromethane from difluoromethane has been achieved using vapour phase contacting. Various other techniques, known in the art, may also be used for contacting the difluoromethane stream with the active carbon particles, for example fluidised or moving beds of adsorbent active Carbon particles. Selection of the particle size and bed shape may be varied within a broad range and may be determined according to known principles and in particular so as to provide the preferred surface areas previously described.

The hourly space velocity of the difluoromethane stream over the active carbon may be varied within a wide range. Generally, difluoromethane may be passed over the active carbon with a gas hourly space velocity of 20 to 3600 $hr^{-1}$, although the gas hourly space velocity may be much greater or much lower than this if desired. The corresponding liquid hourly space velocity for liquid phase operation is 1 to 30 $hr^{-1}$.

The temperature at which the vapour phase process is carried out will typically be between $-50$ and 100° C. and conveniently from 0° C. to 50° C., especially room temperature. The pressure will be dependent to some extent upon whether liquid or vapour phase contacting is chosen but may be between 0.1 and 30 bar, for example.

The active carbon bed will require regeneration or reactivation when its absorption capacity has been filled. Regeneration may be by passing a gas stream, typically nitrogen or air, over the active carbon bed at elevated temperature, for example from about 150° C. to about 400° C., to desorb the chlorocarbon.

The invention is illustrated but not limited by the following examples.

EXAMPLE 1.

500 $cm^3$ of active carbon (Grade 100CTC, Mesh 10-30) was packed into a pressure vessel (Whitey bomb) of diameter 5 cms and length 30 cms. 2.2 kg of difluoromethane was passed over the active carbon at a flow rate of 4-5 g/minute at room temperature and pressure. The hourly space velocity was 200 $hr^{-1}$. The product was collected in a container cooled by a dry ice/trichloroethylene mixture.

The amount of impurities present in the difluoromethane before and after passing over the active carbon bed were determined by Gas Chromatography and the results are shown in Table 1.

TABLE 1

|  | Before Purification | After Purification |
|---|---|---|
| $CH_2Cl_2$ | 252 ppm | 5 ppm |
| $CH_3Cl$ | 95 ppm | 45 ppm |
| $CH_2ClF$ | 245 ppm | 9 ppm |
| $CHF_2Cl$ | 31 ppm | 14 ppm |

EXAMPLES 2 to 7

The following procedure was carried out with 6 different active carbons. For the purposes of comparison, two runs were carried out with unactivated carbons.

10 g of the selected carbon was placed in a polypropylene tube of ⅜ inch internal diameter and a vapour mixture of difluoromethane, chlorofluoromethane and dichlorodifluoromethane, having the composition detailed in Table 2 was passed over the carbon with a flow rate of 60 ml/minute. The off gases from the tube after contact with the carbon were sampled at regular intervals of time and the samples analysed by Gas Chromatography. The results are shown in Table 2(a)–(h) in which all compositions are given in % based on Gas Chromatograph peak areas only.

TABLE 2 (a)

| Time (minutes) | Composition (%) | | | |
|---|---|---|---|---|
|  | $CH_2F_2$ | $CH_2FCl$ | $CF_2Cl_2$ | $CF_3CH_3$ |
| 0 (Feed) | 99.31 | 0.28 | 0.20 | 0.18 |
|  | 99.99 | 0.00 | 0.00 | 0.03 |
| 5 | 99.99 | 0.00 | 0.00 | 0.03 |
| 30 | 99.99 | 0.00 | 0.00 | 0.07 |
| 60 | 99.97 | 0.00 | 0.00 | 0.14 |
| 90 | 99.84 | 0.00 | 0.01 | 0.18 |
| 120 | 99.76 | 0.00 | 0.04 | 0.18 |
| 180 | 99.62 | 0.01 | 0.16 | 0.18 |

TABLE 2 (b)

| Time (minutes) | Composition (%) | | | |
|---|---|---|---|---|
|  | $CH_2F_2$ | $CH_2FCl$ | $CF_2Cl_2$ | $CF_3CH_3$ |
| 0 (Feed) | 99.60 | 0.13 | 0.10 | 0.13 |
| 5 | 99.99 | 0.00 | 0.00 | 0.02 |
| 60 | 99.97 | 0.00 | 0.00 | 0.09 |
| 90 | 99.81 | 0.00 | 0.01 | 0.13 |
| 120 |  | 0.00 | 0.03 | 0.13 |
| 150 |  | 0.01 | 0.05 | 0.13 |

TABLE 2 (c)

| Time (minutes) | Composition (%) | | | |
|---|---|---|---|---|
|  | $CH_2F_2$ | $CH_2FCl$ | $CF_2Cl_2$ | $CF_3CH_3$ |
| 0 (Feed) | 99.64 | 0.10 | 0.10 | 0.13 |
| 5 | 99.99 | 0.00 | 0.00 | 0.00 |
| 60 | 99.95 | 000 | 0.00 | 0.01 |
| 90 | 99.86 | 0.00 | 0.02 | 0.10 |
| 120 | 99.80 | 0.01 | 0.04 | 0.12 |

TABLE 2 (d)

| Time (minutes) | Composition (%) | | | |
|---|---|---|---|---|
|  | $CH_2F_2$ | $CH_2FCl$ | $CF_2Cl_2$ | $CF_3CH_3$ |
| 0 (Feed) | 99.33 | 0.28 | 0.20 | 0.18 |
| 5 | 99.98 | 0.00 | 0.00 | 0.01 |

TABLE 2 (d)-continued

| Time (minutes) | Composition (%) | | | |
|---|---|---|---|---|
|  | $CH_2F_2$ | $CH_2FCl$ | $CF_2Cl_2$ | $CF_3CH_3$ |
| 30 | 99.91 | 0.01 | 0.02 | 0.06 |

TABLE 2 (e)

| Time (minutes) | Composition (%) | | | |
|---|---|---|---|---|
|  | $CH_2F_2$ | $CH_2FCl$ | $CF_2Cl_2$ | $CF_3CH_3$ |
| 0 (Feed) | 99.66 | 0.08 | 0.09 | 0.13 |
| 5 | 99.98 | 0.00 | 0.00 | 0.04 |
| 30 | 99.95 | 0.00 | 0.01 | 0.09 |
| 60 | 99.85 | 0.01 | 0.02 | 0.12 |

TABLE 2 (f)

| Time (minutes) | Composition (%) | | | |
|---|---|---|---|---|
|  | $CH_2Cl_2$ | $CH_2FCl$ | $CF_2Cl_2$ | $CF_3CH_3$ |
| 0 (Feed) | 99.59 | 0.13 | 0.10 | 0.13 |
| 5 | 99.98 | 0.00 | 0.00 | 0.01 |
| 30 | 99.98 | 0.00 | 0.00 | 0.07 |
| 60 | 99.90 | 0.00 | 0.01 | 0.12 |
| 90 | 99.92 | 0.01 | 0.03 | 0.13 |

TABLE 2 (g)

| Time (minutes) | Composition (%) | | | |
|---|---|---|---|---|
|  | $CH_2F_2$ | $CH_2FCl$ | $CF_2Cl_2$ | $CF_3CH_3$ |
| 0 (Feed) | 99.42 | 0.21 | 0.16 | 0.18 |
| 5 | 99.75 | 0.01 | 0.02 | 0.18 |

TABLE 2 (h)

| Time (minutes) | Composition (%) | | | |
|---|---|---|---|---|
|  | $CH_2F_2$ | $CH_2FCl$ | $CF_2Cl_2$ | $CF_3CH_3$ |
| 0 (Feed) | 99.59 | 0.13 | 0.10 | 0.13 |
| 5 | 9.70 | 0.07 | 0.09 | 0.04 |

The active carbons tested were as follows:
1. Grade AR2, surface area >1200 m²/g: Table 2(a)
2. Grade 607C, surface area >1100 m²/g: Table 2(b)
3. Grade 100CTC: surface area unknown: Table 2(c).
4. Grade 209M, surface area 900 m²/g: Table 2(d)
5. Grade 208C, surface area 1100 m²/g: Table 2(e).
6. Grade BR1, surface area 1000 m²/g: Table 2(f).
Comp 1. Unactivated animal charcoal: Table 2(g).
Comp 2. Unactivated lumpwood charcoal: Table 2(h).

All active carbons were supplied by Sutcliffe Speakman Carbons Ltd.

I claim:
1. A process for the removal of chlorocarbon impurities from difluoromethane which comprises contacting the impure difluoromethane with active carbon at a temperature of from about −50° C. to about 100° C.
2. A process as claimed in claim 1 wherein said chlorocarbon impurity is chlorofluoromethane.
3. A process as claimed in claim 1 wherein the active carbon is a coconut or coconut shell activated carbon.
4. A process as claimed in any one of claims 1 to 3 wherein the active carbon has a surface area of at least about 1000 m²/g.
5. A process as claimed in claim 4 wherein the active carbon has a surface area of at least about 1100 m²/g.
6. A process as claimed in claim 4 wherein impure difluoromethane in the vapour phase is contacted with the active carbon.

* * * * *